United States Patent [19]

Mugrage

[11] Patent Number: 5,576,439
[45] Date of Patent: Nov. 19, 1996

[54] DIHYDROPYRIDINECARBOXYLIC ACID ANHYDRIDES

[75] Inventor: Benjamin B. Mugrage, Basking Ridge, N.J.

[73] Assignee: Ciba-Geigy Corporation, Tarrytown, N.Y.

[21] Appl. No.: 331,071

[22] Filed: Oct. 28, 1994

[51] Int. Cl.⁶ .................. C07D 213/79; C07D 213/80; A61K 31/44
[52] U.S. Cl. ............................................. 546/263
[58] Field of Search ........................... 546/263; 514/332

[56] References Cited

U.S. PATENT DOCUMENTS

| | | | |
|---|---|---|---|
| 4,285,955 | 8/1981 | Wehinger et al. | 424/266 |
| 4,672,068 | 6/1987 | Kutsuma et al. | 514/336 |
| 4,672,071 | 6/1987 | Clark et al. | 514/356 |
| 4,999,362 | 3/1991 | Gandolfi et al. | 514/334 |

OTHER PUBLICATIONS

Chem. Pharm. Bull., vol. 9, No. 1, 1991, pp. 108–111.
Bisorganic & Medicinal Chemistry Letters, vol. 3, No. 10, pp. 2099–2104, 1993.
J. Clin. Invest., vol. 93, May 1994, pp. 2141–2148.
Experimental Biol. '94, Apr. 24–28, 1994 Anaheim, CA, Poster Presentation.
Chem. Pharm. Bull., vol. 39, No. 1, pp. 108–111 1991.

*Primary Examiner*—Alan L. Rotman
*Attorney, Agent, or Firm*—Norbert Gruenfeld

[57] ABSTRACT

The invention relates to the compounds of formula I

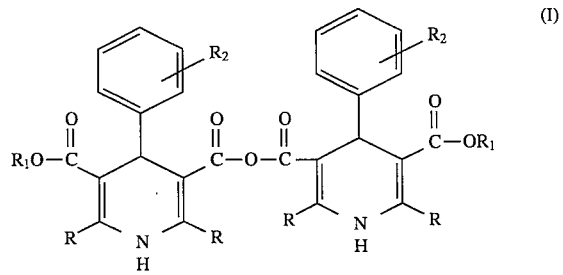

wherein R is lower alkyl or hydrogen; $R_1$ is hydrogen, lower alkyl or aryl-lower alkyl; $R_2$ is hydrogen, nitro, cyano trifluoromethyl, halo, lower alkoxy, lower alkyl, lower alkoxycarbonyl, aminocarbonyl or mono- or di-lower alkylaminocarbonyl, amino or mono- or di-lower alkylamino; and pharmaceutically acceptable salts thereof when $R_1$ is hydrogen; which are useful as endothelin antagonists.

11 Claims, No Drawings

DIHYDROPYRIDINECARBOXYLIC ACID ANHYDRIDES

SUMMARY OF THE INVENTION

The present invention relates to dihydropyridine carboxyclic acid anhydrides useful as endothedin (ET) receptor antagonists, in particular ET-1 antagonists, methods for preparation thereof, pharmaceutical compositions comprising said compounds, a method of inhibiting endothelin activity in mammals and a method of treating endothelin dependent diseases or conditions in mammals using such compounds or pharmaceutical compositions comprising such compounds.

Elevated levels of endothelin have been reported to be found in essential hypertension, myocardial infraction, atherosclerosis, cerebral ischemia. Endothelin is also known to be, inter alia, a potent constrictor of mammalian bronchial tissue.

Thus, the endothelin receptor antagonists of this invention are expected to be useful in the treatment of e.g. hypertension, myocardial and cerebral ischemia, heart failure, and bronchial disorders, such as asthma.

DETAILED DESCRIPTION OF THE INVENTION

The present invention relates to the compounds of formula I

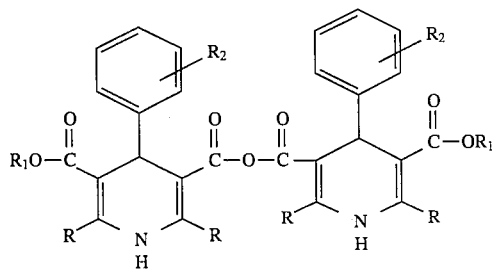

wherein R is lower alkyl or hydrogen; $R_1$ is hydrogen, lower alkyl or aryl-lower alkyl; $R_2$ is hydrogen, nitro, cyano, trifluoromethyl, halo, lower alkoxy, lower alkyl, lower alkoxycarbonyl, aminocarbonyl or mono- or di-lower alkylaminocarbonyl, amino or mono- or di-lower alkylamino; and pharmaceutically acceptable salts thereof when $R_1$ is hydrogen.

The compounds of the invention exist in the form of diastereomers (with respect to the two 4-dihydropyridyl asymmetric centers), namely the meso isomer and racemate or mixtures thereof. The racemate in turn consists of the R,R and S,S enantiomers. All are within the purview of the invention. Preferred are the meso and S,S isomers.

Preferred are the compounds of formula I wherein R is $C_1$–$C_4$-straight chain alkyl; $R_1$ is lower alkyl; and $R_2$ is hydrogen, nitro, lower alkoxy, trifluoromethyl or halo.

Preferred are said compounds of formula I wherein all R, $R_1$ and $R_2$ substituents are identical; R is methyl; $R_1$ is methyl or ethyl; $R_2$ is hydrogen, nitro, trifluoromethyl, chloro, methyl or methoxy.

Preferred are the above compounds wherein $R_2$ is located at the meta position.

Also preferred are any of the said compounds in substantially pure form.

The general definitions used herein have the following meaning within the scope of the present invention, unless otherwise specified.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1–4 carbon atoms, and represents for example methyl, ethyl, propyl, butyl, isopropyl or isobutyl.

A lower alkoxy (or alkyloxy) group preferably contains 1–4 carbon atoms, advantageously 1–3 carbon atoms, and represents for example ethoxy, propoxy, isopropoxy, or most advantageously methoxy.

Halogen (halo) preferably represents chloro or fluoro but may also be bromo or iodo.

Aryl represents preferably phenyl or phenyl monosubstituted by lower alkoxy, halogen, lower alkyl or trifluoromethyl, especially phenyl or phenyl monosubstituted by lower alkoxy, halogen or trifluoromethyl, and in particular phenyl.

Aryl-lower alkyl represents preferably straight chain or branched aryl-$C_1$–$C_4$-alkyl in which aryl has meaning as defined above, e.g. benzyl or phenyl-(ethyl, propyl or butyl), each unsubstituted or substituted on phenyl ring as defined under aryl above, advantageously optionally substituted benzyl.

Lower alkoxycarbonyl represents preferably $C_1$–$C_4$-alkoxycarbonyl, e.g. ethoxycarbonyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-ammonium salts.

The compounds of the invention exhibit ET-1 antagonist activity with selectivity for the $ET_A$ receptor and are useful as positive controls in tests for the evaluation and discovery of new potential ET-1 antagonists and their selectivity for the $ET_A$ receptor.

The compounds of the invention are also useful for reducing or blocking endothelin-$1_A$ receptor activity in mammals.

The compounds of the invention are further useful for the treatment of endothelin-$1_A$ dependent disorders or conditions, e.g. hypertension, and bronchial asthma.

The above-cited properties are demonstrable in in vitro and in vivo tests, using advantageously mammals, e.g. rats, guinea pigs, dogs, rabbits, or isolated organs and tissues, as well as mammalian enzyme preparations. Said compounds can be applied in vitro in the form of solutions, e.g. preferably aqueous solutions, and in vivo either enterally or parenterally, advantageously intravenously e.g. in aqueous solution. The dosage in vitro may range between about $10^{-5}$ molar and $10^{-10}$ molar concentrations. The dosage in vivo may range, depending on the route of administration, between about 0.01 and 50 mg/kg.

The beneficial biological effects can be determined in tests already generally known in the art.

For instance the $ET_A$ receptor inhibitory activity can be determined by measuring the release of [$^3$H]-inositol from [$^3$H]-inositol labeled A7r5 cells, as previously described by Cioffi et at, J. Cardiovasc. Pharmacol. 22 (Suppl. 8), S-168 (1993).

Illustrative of the invention, the compound of example 1 inhibits the binding of [$^{125}$I] ET-1 to the $ET_A$ receptor in the above test with an $IC_{50}$ of about 140 nM.

Inhibition of the binding of [$^{125}$I] ET-1 to porcine thoracic aorta membranes ($ET_A$ receptor) is determined according to Cioffi et al, J. Pharmacol. Exp. Ther. 262, 611 (1992); similarly inhibition of binding of [$^{125}$I] ET-1 to rat cerebellum membranes (ET$_B$ receptor).

Illustrative of the invention, the compound of example 1 inhibits [$^{125}$I] ET-1 binding to ET$_A$ receptors in porcine thoracic aorta membranes with an IC$_{50}$ of about 16 nM and inhibits [$^{125}$I] ET-1 binding to ET$_B$ receptors in rat cerebellar membranes with an IC$_{50}$ of about 300 nM.

The cardiovascular effects of ET-1 inhibitory activity can be determined as follows:

A 30 minute pretreatment with test compound (0.1–10 µM) is utilized to determine inhibition of the ET-1 induced contractile response in isolated rabbit aorta. The maximal response to ET-1 is measured at 0.1, 1 and 10 µM, respectively. Similar pretreatment with test compound (1 µM) is utilized to determine the effects of phenylephrine or KCl induced contraction, an indication that the specificity of hemodynamic affects is caused by intereaction with the endothelin receptor. A 5 minute pretreatment with test compound (10 mg/kg, i.v.) is also used to assess the effects on pressor response and attenuation of the depressor response to ET-1 (0.25 nmol/kg iv.) in the conscious rat.

Illustrative of the invention, pretreatment with the compound of example 1 (10 mg/Kg i.v.) completely antagonizes the increase in blood pressure induced by ET-1 (0.25 nM/Kg i.v.) in the conscious rat. The compound of example 1 also inhibits the ET-1 induced contractile response in isolated rabbit aorta by 77% at a concentration of 10 µM.

The compounds of formula I can be prepared e.g. by reacting a carboxylic acid of formula II (II)

wherein R and R$_2$ have meanings as defined above and R$_1$ represents lower alkyl or aryl-lower alkyl, with a dehydrating agent, and, if desired, separating the resulting mixture of isomers.

Suitable dehydrating agents are those known in the art for anhydride formation such as carbodiimides, e.g. dicyclohexylcarbodiimides or 1-ethyl-3-(3-dimethylaminopropyl) carbodiimide HCl CEDCD, optionally with a catalytic amount of a tertiary amine (such as dimethylaminopyrridine (DMAP)), oxalyl chloride in the presence of a tertiary amine (e.g. pyridine), or diethyl azodicarboxylate (DEAD) in the presence of triphenylphosphine.

The reaction is carried out under conditions well-known in the art, e.g. in the presence of inert solvents (e.g. methylene chloride, dimethylformamide), preferably at room temperature.

Separation of the isomers is carded out by fractional crystallization or chromatographic separation, e.g. flash chromatography on silica gel.

The racemic or optically active starting materials of formula II are known or are prepared according to methods known in the art, e.g. according to U.S. Pat. No. 4,285,955 and Chem. Pharm. Bull. 39, 108 (1991). The racemate may be resolved into the optical antipodes using methods well known in the art.

Depending on the nature of the starting material of formula II with respect to the asymmetric center at position 4 of the dihydropyridine ting, the product may either be a mixture of the meso and racemic diastereomers (which can be separated into the individual diastereomers), the R,R-enantiomer or the S,S-enantiomer.

For instance the racemic starting material of formula II would yield a mixture of the meso and racemic diastereomers from which each of the individual diastereomers can be isolated. The R-isomer of formula II in turn would yield the S,S-enantiomer of formula I and the S-isomer of formula II would yield the R,R-enantiomer of formula I. The R,R and S,S enantiomers can also be obtained by resolution of the racemate.

Finally, acidic compounds of the invention are either obtained in the free form, or as a salt thereof.

Acidic compound of the invention may be converted into salts with equivalent amounts of pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals to inhibit endothelin and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Tablets and gelatin capsules comprise the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants,e.g. starches, agar, alginic acid or its sodium salt, or effervescent mixtures; and/or 3) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional methods and contain about 0.1 to 75%, preferably about 1 to 50%, of the active ingredient.

The dosage of active compound administered is dependent on the species of warm-blooded animal (mammal), the body weight, age and individual condition, and on the form of administration. A unit dosage for oral administration to a mammal of about 50 to 70 kg may contain between about 1 and 100 mg of the active ingredient.

The present invention also relates to methods of using the compounds of the invention and their pharmaceutically acceptable salts, or pharmaceutical compositions thereof, in mammals for inhibiting endothelin, in particular endothelin-$1_A$, and for the treatment of endothelin dependent conditions as described herein, e.g. hypertension, myocardial ischemia, bronchial disorders in mammals.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLE 1

(a) 1,4-Dihydro-5-methoxycarbonyl-2,6-dimethyl-4-(3-nitrophenyl)-3-pyridinecarboxylic acid [A. Ashimori, T. Uchida, Y. Ohtaki, M. Tanaka, K. Oho, C. Fukaya, M. Watanabe, M. Kagitani and K. Yokoyama; Chem. Pharm. Bull, 39, 108, (1991)] (21.4 g, 0.065 mol) and 1-ethyl-3-(3-dimethylaminopropyl)-carbodiimide hydrochloride (23.0 g., 0.120 mol) are suspended in dry $CH_2Cl_2$ (300 ml) and treated with a catalytic amount (25 mg) of 4-dimethylaminopyridine. The reaction is stirred at room temperature, under an $N_2$ atmosphere, until a clear yellow solution is obtained (about 2 hours). The solution is transferred to a separatory funnel and washed sequentially with water (200 ml), 1 N $K_2CO_3$ (100 ml) and brine (100 ml). The organic layer is dried ($MgSO_4$) and concentrated to a yellow foam. The crude product is purified by passing through a short plug of flash silica gel, eluted with 1:1 $Et_2O$/EtOAc followed by EtOAc to produce, after evaporation, a 2:1 mixture of diastereomers favoring the meso-isomer. The isomeric mixture is then dissolved in THF (600 ml) and $Et_2O$ added until the solution becomes slightly cloudy. The solution is kept at 4° C. overnight to give meso-1,4-dihydro-5-methoxycarbonyl-2,6-dimethyl-4-(3-nitrophenyl)-3-pyridine-carboxylic acid anhydride as a light yellow solid, m.p. 223°–224° C. dec., of the formula

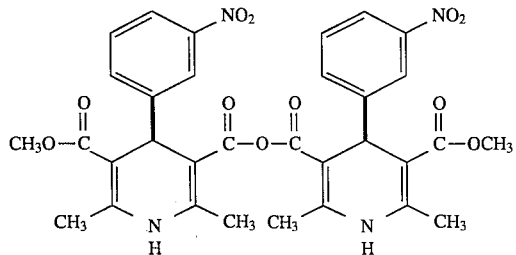

$^1$H-NMR (DMSO-$d_6$) 9.38 s, 2H: 8.03, d, 2H, J=8.3; 7.70, s, 2H; 746–7.57, m, 4H; 4.58, s, 2H; 3.50, s, 6H; 2.26, s 6H; 2.19, s, 6H, $^1$H-NMR (CDCL$_3$) 8.00, m, 2H; 7.85, m, 2H; 7.85, m 2H; 7.33–750, m 4H; 5.95, s 2H, 4.72, s, 2H; 3.60, 6H; 2.30, s, 6H; 2.26, s, 6H.

(b) Similarly prepared from (R)- 1,4-dihydro-5-methoxycarbonyl-2,6-di-methyl-4-(3-nitrophenyl) 3-pyridinecarboxylic acid is (S,S)-1,4-di-hydro-5-methoxycarbonyl-2,6-dimethyl-4-(3-nitrophenyl)-3-pyridinecarboxylic acid anhydride, m.p. 130° C., of the formula

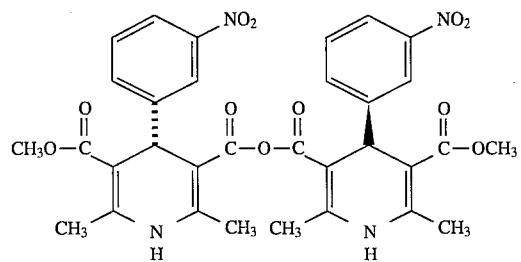

(c) Similarly prepared from (S)-1,4-dihydro-5-methoxycarbonyl-2,6-dimethyl-4-(3-nitrophenyl) 3-pyridinecarboxylic acid is (R,R)-1,4-dihydro-5-methoxy-carbonyl-2,6-dimethyl-4-(3-nitrophenyl)-3-pyridinecarboxylic acid anhydride, m.p. 130°–132° C., of the formula

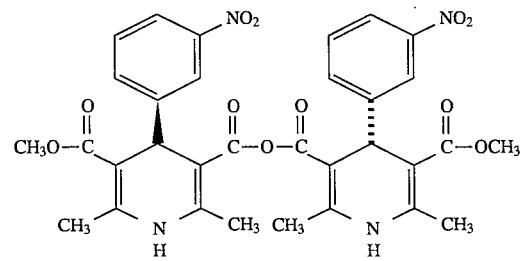

EXAMPLE 2

Prepared similarly to the compounds in example 1 are:

(a) 1,4-Dihydro-5-methoxycarbonyl-2,6-dimethyl-4-(3-chlorophenyl)-3-pyridine-carboxylic acid anhydride as a mixture of isomers, m.p. 108°–110° C.

(b) 1,4-Dihydro-5-methoxycarbonyl-2,6-dimethyl-4-phenyl-3-pyidinecarboxylic acid anhydride as a mixture of isomers, m.p. 132° C..

(c) 1,4-Dihydro-5-methoxycarbonyl-2,6-dimethyl-4-(3-methoxyphenyl)-3-pyridine-carboxylic acid anhydride, as a mixture of isomers, m.p. 99°–101° C.

What is claimed is:

1. A compound of the formula

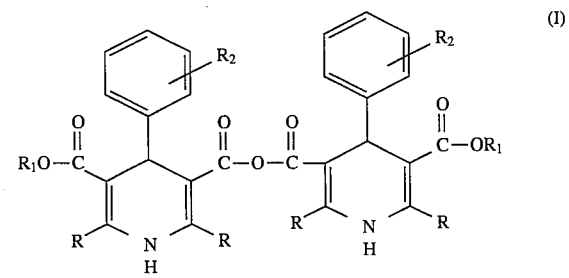

(I)

wherein R is lower alkyl or hydrogen; $R_1$ is hydrogen, lower alkyl or aryl-lower alkyl; $R_2$ is hydrogen, nitro, cyano trifluoromethyl, halo, lower alkoxy, lower alkyl, lower alkoxycarbonyl, aminocarbonyl or mono- or di-lower alkylaminocarbonyl, amino or mono- or di-lower alkylamino; or a pharmaceutically acceptable salt thereof when $R_1$ is hydrogen.

2. A compound according to claim 1 of formula I wherein R is $C_1$–$C_4$-straight chain alkyl; $R_1$ is lower alkyl; and $R_2$ is hydrogen, nitro, lower alkoxy, trifluoromethyl or halo.

3. A compound according to claim 1 of formula I wherein all R, $R_1$ and $R_2$ substituents are identical; R is methyl; $R_1$ is methyl or ethyl; and $R_2$ is hydrogen, nitro, trifluoromethyl, chloro, methyl or methoxy.

4. A compound according to claim 1 which is the meso diastereomer.

5. A compound according to claim 1 which is the S,S isomer.

6. A compound according to claim 1 wherein $R_2$ is located at the meta position.

7. A compound according to claim 6 being 1,4-dihydro-5-methoxy-carbonyl-2,6-dimethyl-4-(3-nitrophenyl) 3-pyridinecarboxylic acid anhydride of formula I wherein R is methyl, $R_1$ is methyl and $R_2$ is m-nitro.

8. A compound according to claim 7 being the meso isomer thereof in substantially pure form.

9. A compound according to claim 6 being 1,4-dihydro-5-methoxy-carbonyl-2,6-dimethyl-4-(3-chlorophenyl) 3-pyridinecarboxylic acid anhydride of formula I wherein R is methyl, $R_1$ is methyl and $R_2$ is m-chloro.

10. A compound according to claim 6 being 1,4-dihydro-5-methoxy-carbonyl-2,6-dimethyl-4-(3-methoxyphenyl) 3-pyridinecarboxylic acid anhydride of formula I wherein R is methyl, $R_1$ is methyl and $R_2$ is m-methoxy.

11. A compound according to claim 6 being 1,4-dihydro-5-methoxy-carbonyl-2,6-dimethyl-4-phenyl 3-pyridinecarboxylic acid anhydride of formula I wherein R is methyl, $R_1$ is methyl and $R_2$ is hydrogen.

* * * * *